United States Patent [19]

Kopetzki et al.

[11] Patent Number: 5,602,018
[45] Date of Patent: Feb. 11, 1997

[54] HYPOGLYCOSYLATED RECOMBINANT GLUCOSE OXIDASES

[75] Inventors: Erhard Kopetzki, Penzberg; Klaus Lehnert, Hammersbach, both of Germany

[73] Assignee: Boehringer Mannheim GmbH, Mannheim, Germany

[21] Appl. No.: 374,770

[22] PCT Filed: Aug. 2, 1993

[86] PCT No.: PCT/EP93/02054

§ 371 Date: Feb. 7, 1995

§ 102(e) Date: Feb. 7, 1995

[87] PCT Pub. No.: WO94/03608

PCT Pub. Date: Feb. 17, 1994

[30] Foreign Application Priority Data

Aug. 7, 1992 [DE] Germany ............... 42 26 095.7
Jan. 25, 1993 [DE] Germany ............... 43 01 904.8

[51] Int. Cl.⁶ ............... C12N 9/04; C12N 1/14; C12P 21/06
[52] U.S. Cl. ............... 435/190; 435/69.1; 435/254.11
[58] Field of Search ............... 435/69.1, 190, 435/254.11

[56] References Cited

U.S. PATENT DOCUMENTS 5,094,951  3/1992  Rosenberg ............... 435/190

OTHER PUBLICATIONS

Ballou et al. (1991) Proc. Natl. Acad. Sci. USA 88:3209–3212.

Primary Examiner—Robert A. Wax
Assistant Examiner—Lisa J. Hobbs
Attorney, Agent, or Firm—Felfe & Lynch

[57] ABSTRACT

Hypoglycosylated recombinant glucose oxidase with a molecular weight of ca. 68–80 kDa, a specific activity of ca. 200 U/mg unit of weight, a carbohydrate portion of ca. 12% which is obtainable by expression of a recombinant DNA containing the GOD gene in the N-glycosylation-defective yeast mutants DSM 7042, DSM 7338, DSM 7160 or DSM 7340 or allelic mutant strains, fermentation and isolation of the enzyme from the culture supernatant or the cells.

2 Claims, 3 Drawing Sheets

HYPOGLYCOSYLATED RECOMBINANT GLUCOSE OXIDASES

The invention concerns a hypoglycosylated recombinant glucose oxidase (GOD EC 1.1.3.4) as well as the production thereof and its use in diagnostic tests.

There are three ways in which a protein can be provided posttranslationally with carbohydrates. A distinction is made between:

N-glycosylation
  N-glycosidic linking of the carbohydrate chain to Asn
O-glycosylation
  O-glycosidic linking of the carbohydrate chain to Thr or Ser
glycosyl-phosphatidyl-inositol anchor (GPI)
  component of some membrane proteins,
  the GPI anchor serves to embed them in the phospholipid membrane.

The glycosylation of proteins is described for example in:
Kukuruzinska, M. A. et al., Ann. Rev. Biochem. 56 (1987) 915–944;
Paulson, C. P., TIBS 14 (1989) 272–276;
Warren, C. E., BFE 7 (1990) 392–395;
Ballou, C. E., In: Strathern, J. N., et al., The Molecular Biology of the Yeast Saccharomyces, Cold Spring Harbor Laboratory, New York, pp. 355–360 (1982).
Kornfeld, R.; Kornfeld, S., Ann. Rev. Biochem 54 (1985) 631–664;
Tanner, W.; Lehle, L., Biochim. Biophys. Acta 906 (1987) 81–99;
Innis, M. A., In: Barr, P. J. et al., Yeast genetic engineering, Butterworths, Stoneham, Mass., pp. 233–246 (1989).

The O-glycosidic carbohydrate structures of yeast proteins consist of an unbranched mannose chain of 1–5 mannose residues. The O-glycosylation begins in the ER (transfer of the first mannose residue) and is completed in the Golgi apparatus.

N-glycosylation takes place in two steps. A core unit of N-acetylglucosamine, mannose and glucose is built on a lipid carrier intermediate and this is transferred in the ER onto Asn residues of glycoproteins. After the protein-bound core unit has been processed (cleavage of the glucose residues and a specific mannose residue in the ER), the sugar structure is elongated in the Golgi apparatus ("outer chain" glycosylation). The structure of the outer chain glycosylation is organism-specific.

Glucose oxidase (GOD EC 1.1.3.4) from *Aspergillus niger* is a naturally secreted N-glycosylated homodimer with a molecular weight of ca. 80 kDa per subunit (SU), 1 FAD as a cofactor/SU and one disulfide bridge/SU. GOD from *A. niger* has a relatively uniform carbohydrate structure (core glycosylation).

The technical production of glucose oxidase from *Aspergillus niger* is, however, difficult. GOD in *Aspergillus niger* is evidently transported into the peroxisomes (Dijken J. P. van and Veenhuis, M., Eur. J. Appl. Microbiol. 9 (1980) 275–283) which impedes the processing. However, under certain conditions the enzyme can also be secreted into the medium (Mischak, H. et al., Appl. Microbiol. Biotech. 21 (1985) 27–31). The yield of GOD is only low in this case. For these reasons many attempts have already been made to recombinantly produce the glucose oxidase from *Aspergillus niger* in *Saccharomyces cerevisiae*. The recombinant GOD from *Saccharomyces cerevisiae* is more thermostable and pH-stable than the native enzyme from Aspergillus (De Baetselier A. et al., Biotechnology 9 (1991) 559–561). Although high yields of enzyme were obtained in the recombinant production, it turned out, however, that the recombinant enzyme is heterogeneous with regard to the portion of carbohydrate and to the molecular weight of 80 to 140 kDa/SU (SU=subunit) due to a non-uniform "outer chain glycosylation" of up to 150 mannose residues. The recombinant enzyme is hyperglycosylated (carbohydrate portion ca. 70% instead of 16% as in the native enzyme) (De Baetselier et al., Biotechnology 9 (1991) 559–561) and therefore has a substantially higher molecular weight (ca. 80–140 kDa/SU) than the native enzyme. This is disadvantageous for the application of GOD especially in diagnostic tests e.g. the hyperglycosylated recombinant enzyme has a lower specific activity in units per unit of weight (ca. 65 U/mg compared to 178 U/mg for the native enzyme from Aspergillus).

Kriechbaum, M. et al., FEBS Lett. 255 (1989) 63–66;
Frederick K. R. et al., J. Biol. Chem. 265 (1990) 3793–3802;
De Baetselier, A. et al., Biotechnology 9 (1991) 559–561;
Whittington, H. et al., Curr. Genet. 18 (1990) 531–536;
Rosenberg, S., WO 89/12675;

The sequence of the glucose oxidase from *Aspergillus niger* is also described in these publications.

The object of the present invention was to avoid these disadvantages and to provide a recombinant glucose oxidase the N-glycosylation of which is as uniform and low as possible (e.g. with a complete or partial defect in the outer chain glycosylation) and with a high specific activity.

This object is achieved by a hypoglycosylated recombinant glucose oxidase with a molecular weight of 68–80 kDa, a specific activity of ca. 200 U/mg unit of weight, a carbohydrate portion of ca. 12% which is obtainable by expression of a recombinant DNA containing the GOD gene from Aspergillus in the N-glycosylation-defective yeast mutants DSM 7042, DSM 7160, DSM 7338 or DSM 7340 or allelic mutant strains thereof, fermentation and isolation of the enzyme from the culture supernatant or the cells.

It was surprisingly found that GOD isolated from N-glycosylation-defective yeast mutants (e.g. ngd29 mutants) is much more stable than the enzyme from *Aspergillus niger* with a comparable portion of carbohydrate, molecular weight (68–80 kDa, preferably 68–75 kDa) and specific activity.

The yeast strains which are suitable for producing the GOD according to the invention and the production thereof are described in the German Patent Application P 42 26 094.9 with the same priority, the contents of which are a subject matter of the disclosure of the present invention.

Such yeast strains are obtainable by [$^3$H]-mannose suicide selection, introduction of one or several selectable markers (auxotrophy requirements and/or resistances) and selection of those strains which, after transformation with the plasmid YEpL/GOD, secrete more than 10 mg/l GOD into the medium after culture under standard conditions and are allelic to the *Saccharomyces cerevisiae* mutants ngd29 (DSM 7042, DSM 7338) or ngd62 (DSM 7160, DSM 7340).

The technique of [$^3$H]-mannose suicide selection essentially comprises:
  mutagenesis (e.g. starting from the wild-type strain X2180-1A, ATCC 26786)
  incubation with [$^3$H]-mannose
  accumulation of hyperglycosylation-defective mutants by storing the cells at −80° C. until the survival rate of the cells falls to 2–3 powers of ten (2–4 months)
  selection for mutants with reduced N-glycosylation on the basis of homologously expressed invertase
  analysis by activity staining and/or immunoprecipitation of secreted invertase and determination of the molecular weight (glycosylation) by SDS-PAGE The auxotrophy markers are introduced by crossing the yeast strains to form diploids (isolation of the zygotes by micromanipulation) and if necessary subsequent sporulation to form haploids (tetrad analysis). The ngd phenotype was determined by activity staining of external invertase by means of native PAGE gels using sucrose and 2,3,4-trinitrophenyltetrazolium chloride as the substrate/glucose reagent.

Determination of an adequate GOD production can be carried out by determining the activity of the GOD secreted into the medium after culture under standard conditions. For this the strain to be tested (GOD transformant), is incubated for 3–4 days while shaking preferably after a selective preculture in complete medium. Yeast extract, Bactopeptone, fructose and maltose are preferably added at neutral pH to the complete medium.

The determination of glucose oxidase is carried out for example according to the method described in the examples under "general methods".

Mutants according to the invention (allelic mutants) can be determined by a test in which the mutants to be tested are analysed whether they have a mutation in the same genes as the yeast strains DSM 7042/7338 (ngd29) and DSM 7160/7340 (ngd62).

For this the strain to be tested is crossed in each case with the yeast strains DSM 7042/7338 and DSM 7160/7340 and the diploid strains obtained in this process are analysed.

The mutation (strain) to be tested is allelic to the ngd mutants according to the invention (DSM 7042/7338, ngd29) and/or (DSM 7160/7340, ngd62) if the mutations do not compensate in diploid cells.

The mutation (strain) to be tested is not allelic to the ngd mutants according to the invention (DSM 7042/7338, ngd29) and/or (DSM 7160/7340, ngd62) if the mutations complement themselves in the diploid cells and a wild-type phenotype results with regard to N-glycosylation.

Yeast strains which are preferably used according to the invention are the strains DSM 7042, DSM 7160, DSM 7338 and DSM 7340. The strains DSM 7338 and DSM 7340 are particularly preferred.

The thermostability was determined on the basis of DSC spectra ("differential scanning calorimetry"). According to this the Tm value is at least 73° C. compared to 68.5° C. for the GOD from *Aspergillus niger*.

After a temperature stress at 55° C. for 2 hours the residual activity of GOD is still at least 30%.

A preferred embodiment of the GOD according to the invention is C-terminal active GOD fusion proteins which contain a plurality of additional histidines or cysteines. Such derivatives are described for example in EP-B 0 184 355 and can be purified in a simple manner.

The invention in addition concerns a process for the production of recombinant glucose oxidase from *Aspergillus niger* in *Saccharomyces cerevisiae* with a uniform carbohydrate structure characterized in that *Saccharomyces cerevisiae* strains with a defect in the ngd29 gene (e.g. DSM 7042/7338) and/or ngd62 gene (e.g. DSM 7160/7340) are transformed with a recombinant DNA which contains the gene for GOD and, after culture of the cells, the glucose oxidase is isolated from the cells or from the supernatant.

Finally the invention in addition concerns the use of a glucose oxidase according to the invention in a diagnostic test.

For patent purposes the following were deposited under the Budapest Treaty at the "Deutsche Sammlung für Mikroorganismen und Zellkulturen GmbH (DSM)", Mascheroder Weg 1 B, D-3300 Braunschweig. Subject to 37 CFR 1.808(b), all restrictions imposed by the depositor on the availability to the public of the deposited material will be irrevocably removed upon granting of the patent.

| | Deposit number | Deposit date |
|---|---|---|
| 1. Plasmid YEpL | DSM 7038 | 07.04.1992 |
| 2. Yeast mutant BMY3-9A (ngd29) | DSM 7042 | 08.04.1992 |
| 3. Yeast mutant BMY3-9C (ngd29) | DSM 7193 | 24.07.1992 |
| 4. Yeast mutant BMY12-20D (ngd62) | DSM 7160 | 09.07.1992 |
| 5. Yeast mutant BMY8-12A (ngd62) | DSM 7157 | 09.07.1992 |
| 6. Yeast mutant BMY13-7B (mnn9) | DSM 7158 | 09.07.1992 |
| 7. Yeast mutant BMY13-1C (mnn9) | DSM 7159 | 09.07.1992 |
| 8. Yeast mutant JM 1935 | DSM 7156 | 09.07.1992 |
| 9. Yeast mutant DBY 746 | DSM 4316 | 14.12.1987 |
| 10. Yeast mutant N-BMY3-9A | DSM 7338 | 08.12.1992 |
| 11. Yeast mutant N-BMY13-1C | DSM 7339 | 08.12.1992 |
| 12. Yeast mutant N-BMY12-20D | DSM 7340 | 08.12.1992 |
| 13. Yeast mutant N-BMY3-9C | DSM 7341 | 08.12.1992 |

Figure 1:
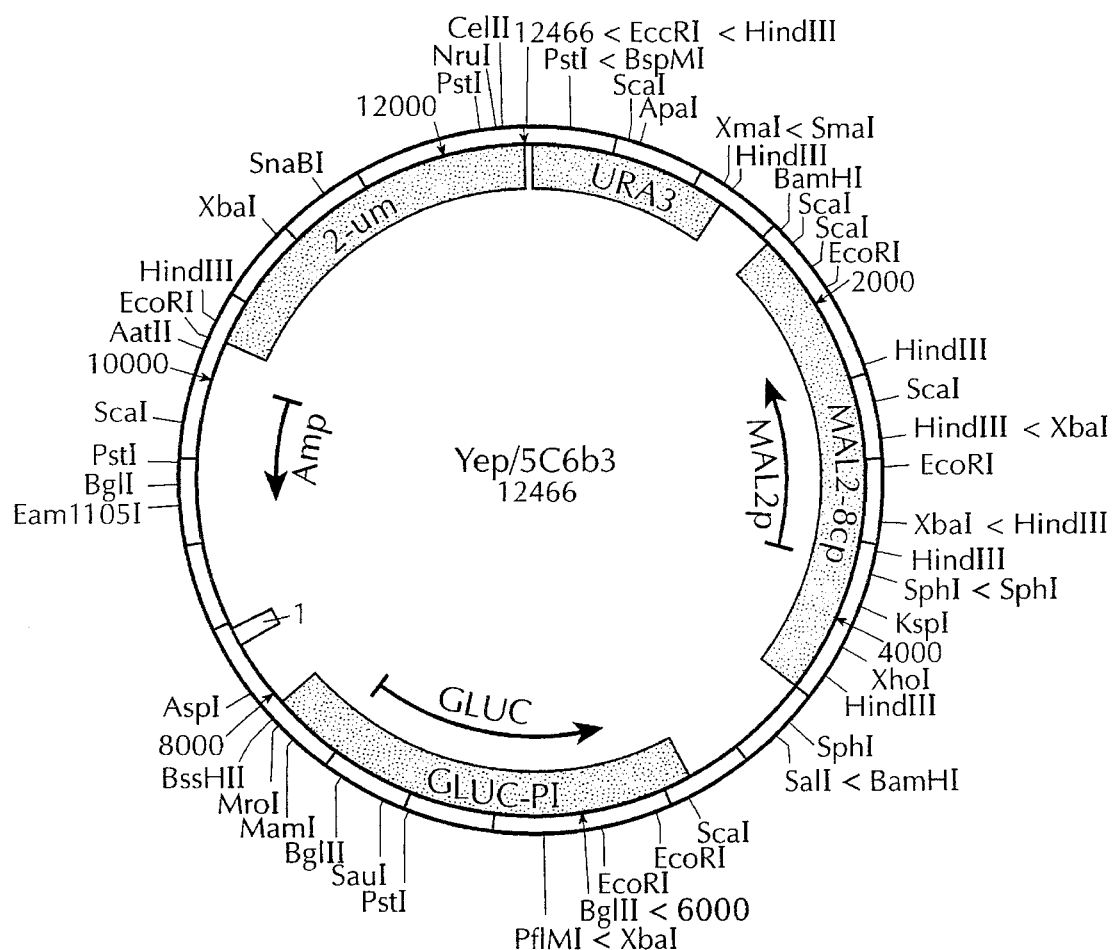
FIG. 1 depicts the plasmid YEp/5C6b3.

The following examples elucidate the invention further.

EXAMPLES

General Methods
Recombinant DNA Technique

Standard methods were used to manipulate DNA such as those described by Maniatis, T. et al., in: Molecular cloning: A laboratory manual. Cold Spring Harbor Laboratory Press, Cold Spring Harbor, N.Y., (1989). The molecular biological reagents used were used according to the manufacturer's instructions.

Yeast Transformation

*Saccharomyces cerevisiae* strains were transformed according to the method of Beggs, J. D. (Nature 275 (1978) 104–109; Ito, H. et al., J. Bacteriol. 153 (1983) 163–168 or Delorme, E. (Applied and Environmental Microbiology 55 (1989) 2242–2246). Fructose was used instead of glucose as a C source.

Determination of Glucose Oxidase Activity

The determination of GOD activity was carried out at 25° C. in a volume of 1 ml in 0.1 mol/l potassium phosphate buffer, pH 7.0 saturated with oxygen containing 0.18 mol/l glucose, 15 units/ml horse-radish peroxidase and 1.75 mmol/l ABTS® glucose reagent. The reaction was started by addition of glucose oxidase (10 μl sample containing GOD diluted to 5–20 mU/ml) and the change in absorbance/min (ΔA/min) was determined at 405 nm ($\epsilon_{405}$=36.8 [mmol$^{-1}$× 1×cm$^{-1}$]). 1 unit (U) GOD activity is defined as the amount of enzyme which oxidizes 1 μmol glucose per min at 25° C. The specific activity of purified *A. niger* GOD is ca. 230 U/mg protein under these test conditions.

Protein Determinations

The protein determination was carried out by the micro-biuret method (Zamenhof, S. et al., Methods Enzymol. 3 (1957) 696–704) with bovine serum albumin as standard.

The protein concentration of purified GOD enzymes was calculated on the basis of the optical density at 280 nm (1 $OD_{280} \cong 1.5$ mg/ml purified GOD).

Cell Lysis and Isolation of Crude Extract

The cells from 5 ml culture medium (ca. 0.1–0.2 g yeast, wet weight) were centrifuged down. The cell pellet was washed once with 10 mmol/l phosphate buffer, pH 7.0 and subsequently lysed with glass beads by homogenization with a Whirlmix (Ciriacy, M., Mut. Res. 29 (1975) 315–326). Afterwards the cells were resuspended/extracted in 2 ml 10 mmol/l phosphate buffer, pH 7.0, the cell debris was removed by centrifugation and the supernatant was processed further as a crude extract.

SDS Polyacrylamide Gel Electrophoresis (SDS-PAGE)

Soluble samples (medium supernatants and cell lysates) were admixed with 1/5 volumes 5×SDS sample buffer (1×SDS sample buffer: 50 mmol/l Tris-HCl, pH 6.8, 1% SDS, 1% mercaptoethanol, 10% glycerol, 0.001% bromophenol blue) and incubated for 5 min at 95° C. Non-soluble proteins of the cell debris fraction were extracted with 2 ml 1×SDS sample buffer and 6–8 mol/l urea, denatured by heating for 5 minutes to 95° C. and separated from insoluble components by centrifugation. Afterwards the proteins were separated by SDS-PAGE (Laemmli, U.K., Nature 227 (1970) 680–685) and stained with Coomassie Brilliant Blue® dye.

Example 1

Construction of Plasmids for the Secretion of *A. niger* GOD in *S. cerevisiae*

Construction of the Yeast Expression Vector YEpL (Starting Vector)

Plasmid YEpL is based on the α-glucosidase vector YEp/5C6b3 (Kopetzki et al., Yeast 5 (1989) 11–24; Kopetzki, et al., EP-A 0 323 838). The ca. 2.3 kBp long EcoRI/PvuII fragment from the plasmid pBR322 (plasmid origin, ampicillin resistance gene) serves to replicate the plasmid in *E. coli*. For replication in yeast the vector contains the ca. 2.2 kBp long EcoRI fragment from the 2 µm DNA of yeast (subcloned from the *E. coli*/yeast shuttle vector YEp24). In addition the vector contains the URA3 and LEU2d gene in order to select the plasmid in auxotrophic yeast strains and an α-glucosidase expression cassette (GLUCPI gene). It consists of the α-glucosidase promoter, a polylinker (cloning site for the genes to be expressed) and the α-glucosidase terminator. In addition the MAL2-8cp gene is present the gene product of which, the MAL2-8cp protein, activates the α-glucosidase promoter. The α-glucosidase promoter is repressed in the presence of glucose. It derepresses after consumption of the glucose and achieves its maximum activity after induction with maltose.

1.1 Construction of the Plasmid YEp/KL6b3

The ca. 1.4 kBp long DNA sequence which is not required between the α-glucosidase terminator and the MAL2-8cp promoter was deleted from the plasmid YEp/5C6b3 (FIG. 1).

For this the plasmid YEp/5C6b3 was linearised with XhoI, the 5' overhanging ends were filled up with Klenow polymerase, the plasmid was re-cleaved with MroI and the 8.7 kBp long MroI/XhoI (blunt) vector fragment was isolated. In a second preparation the plasmid YEp/5C6b3 was disgested with the restriction endonucleases MroI and ScaI, the 2.5 kBp long MroI/ScaI fragment containing the α-glucosidase gene was isolated and ligated with the 8.7 kBp long MroI/XhoI(blunt) vector fragment. The desired plasmid was identified by restriction mapping and designated YEp/KL-6b3.

1.2 Construction of the Plasmid YEp/KL-6b3M

A MluI-linker (5'-GACGCGTC-3') was ligated into the SspI restriction endonuclease cleavage site of the 5' non-translated region of the MAL2-8cp gene. Plasmid construction: YEp/KL-6b3M.

1.3 Construction of the Plasmid YEp/KL-6b3M-MCS

The structural gene of α-glucosidase was removed by the "polymerase chain reaction" (PCR) technique (Mullis, K. B. and Faloona, F. A., Methods in Enzymol. 155 (1987) 335–350) and replaced by a DNA linker (multicloning site, MCS).

For this the GLUCPI promoter sequence from the plasmid YEp/KL-6b3M was amplified by means of PCR using the primer pair (see SEQ ID NO. 1 and SEQ ID NO. 2)

Primer (1): 5'-ATTTCTCCTTATTGCGCGCTT- 3'
Primer (2): 5'-TCTATTCAGCTGTCGACATAGATCTTATGTAATTTAGTTACGCTTGAC-3' and the ca. 410 Bp long PCR product was isolated by agarose gel electrophoresis.

The GLUCPI terminator sequence from the plasmid YEp/KL-6b3M was amplified in a second PCR reaction using the primer pair (see SEQ ID NO. 3 and SEQ ID NO.4)

Primer (3): 5'-AGATCTATGTCGACAGCTGAATAGATAAAATTAGTGCGGACTTTTTTTTA-3'

Primer (4): 5'-GTCATTTGTAAAGTAAAATTCCAA-3' and the ca. 860 Bp long PCR product was isolated by agarose gel electrophoresis.

Afterwards equimolar amounts (ca. 50 pg of each) of the isolated PCR fragments were combined in the PCR reaction mixture, incubated for 5 min at 95° C. to denature the ds-DNA, the reaction mixture was cooled to 60° C. to anneal the complementary single DNA strands containing MCS, the hybridization products were converted into ds-DNA using Taq polymerase and amplified in a third PCR reaction using the primer pair (see SEQ ID NO. 1 and SEQ ID NO. 4)

Primer (1): 5'-ATTTCTCCTTATTGCGCGCTT-3'

Primer (4): 5'-GTCATTTGTAAAGTAAAATTCCAA-3'.

Afterwards the ca. 1.27 kBp long PCR product was digested with the restriction endonucleases MroI and MluI, the ca. 0.92 kBp long MroI/MluI-GLUPI-promoter/MCS/GLUCPI terminator fragment was isolated by agarose gel electrophoresis and ligated into the ca. 8.55 kBp long MroI/MluI-YEp/KL-6b3M vector fragment. The desired plasmid YEp/KL-6b3M-MCS was identified by means of restriction mapping and the DNA regions synthesized by means of PCR were checked by DNA sequencing.

1.4 Construction of the Plasmid YEpL

Figure 2:
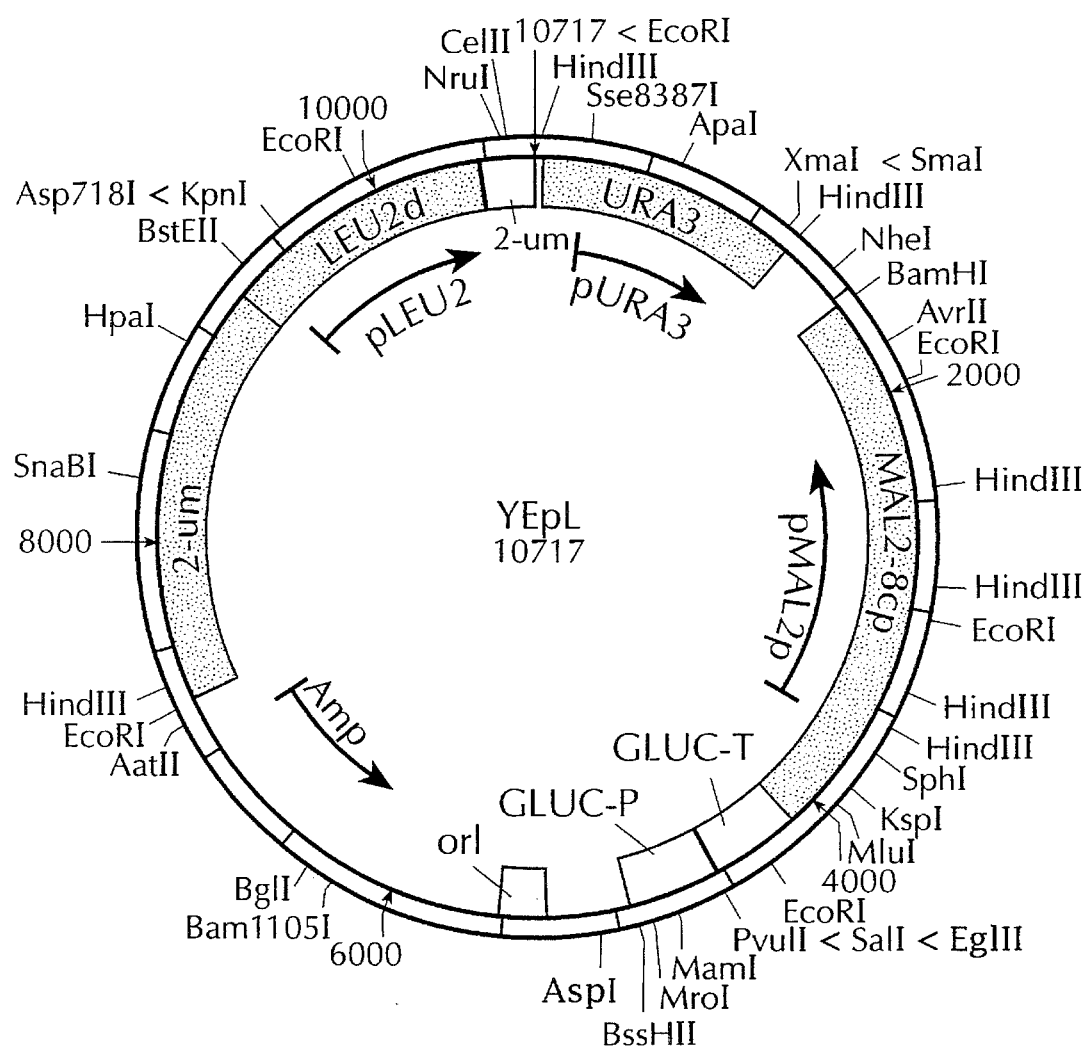
FIG. 2 depicts the plasmid YEpL.

In the following plasmid construction the LEU2d gene was inserted into the plasmid YEp/KL-6b3M-MCS. For this the plasmid YEp/KL-6B3M-MCS was digested with CelII and SnaBI and the 8.4 kBp long CelII/ScaBI-YEp/KL-6b3M-MCS vector fragment was isolated. The LEU2d gene was isolated as a ca. 2.32 kBp long CelII/SnaBI fragment from the plasmid pADH040-2 (Erhart, E. and Hollenberg, C. P., J. Bacteriol. 156 (1983) 625–635) and ligated with the 8.4 kBp long CelII/SnaBI-YEp/KL-6b3M-MCS vector fragment. The desired plasmid construction YEpL (DSM 7038) was identified by restriction mapping (FIG. 2).

1.5 Construction of the Plasmid YEpL/GOD

The cloning of the glucose oxidase gene used (strain: NRRL-3, ATTC 9029), subcloning in the pBluescript SK(+) vector, DNA sequencing and deduction of the GOD protein sequence are described in the publication of Kriechbaum, M. et al. (FEBS Lett. 255 (1989) 63–66). The GOD gene was cloned in 2 partial regions (SalI restriction fragments) into pBluescript SK(+).

The plasmid pSK/GOD-1.8 contains a ca. 1.8 kBp long SalI fragment which codes for the 5'-non-translated region and N-terminal region of the GOD structural gene up to the SalI cleavage site at Bp position 164 (Bp position corresponds to the numbering by Kriechbaum, M. et al). The plasmid pSK/GOD-2.0 contains a ca. 2.0 kBp long SalI fragment which codes for the remainder of the GOD structural gene from Bp position 165 to 1853 as well as for the 3'-non-translated region downstream of the GOD structural gene.

The 5'- and 3'-non-translated region of the GOD gene was removed by means of the PCR technique, both ends of the GOD structural gene were provided with single restriction endonuclease cleavage sites (BglII and PvuII) and in addition a single SphI and NheI cleavage site were introduced into the C-terminal coding region of the GOD structural gene while maintaining a DNA sequence coding for the native GOD protein. Subsequently the GOD structural gene was assembled from the two PCR fragments in a three-fragment ligation and inserted into the vector YEpL. The following primer pair (see SEQ ID NO. 5 and SEQ ID NO. 6) was used to amplify the N-terminal GOD structural gene and plasmid pSK/GOD-1.8 was used as template DNA.

Primer (5): 5'-GCCCGGTACC<u>AGATCT</u>ATGCAGACTCTCCTTGTGAGCT-3'

Primer (6): 5'-TCTAGAACTAGTGGATCCCCC-3'

The following primer pair (see SEQ ID NO. 7 and SEQ ID NO. 8) was used to amplify the remaining GOD structural gene and plasmid pSK/GOD-2.0 was used as template DNA.

Primer (7): 5'-GCCGGCGAACGTGGCGAGAA-3'

Figure 3:
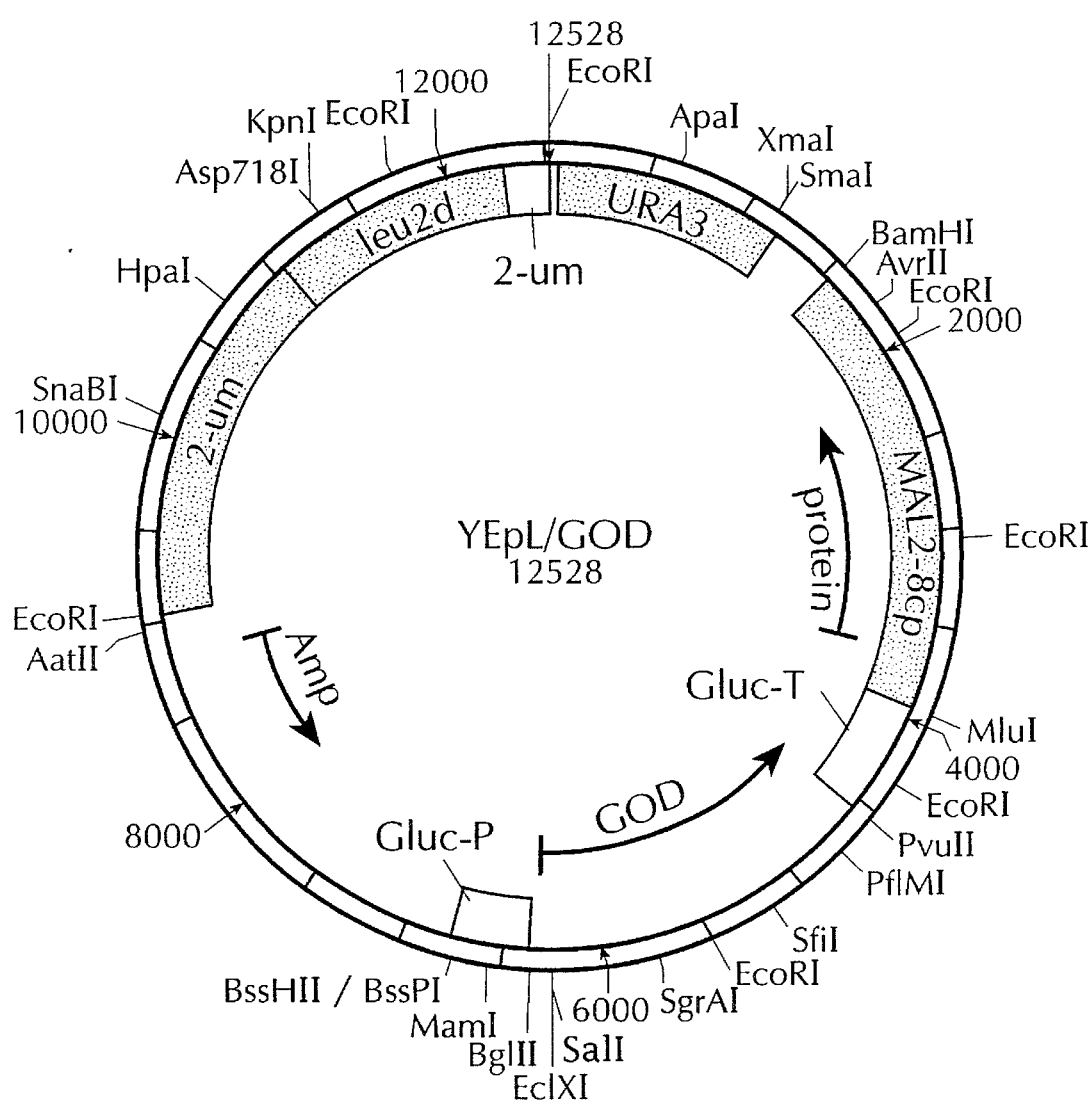
FIG. 3 depicts the plasmid YEp/GOD.

Primer (8): 5'-ATATAT<u>CAGCTG</u>TCACTG<u>CATGC</u>T<u>AGC</u>ATAATCTTCCAAGATAGC-3'
                   PvuII        SphI  NheI The ca. 220 Bp long PCR product of the first reaction was re-cleaved with BglII and SalI and the ca. 130 Bp long BglII/SalI fragment was isolated. The ca. 2.05 kBp long PCR product of the second reaction was digested with SalI and PvuII and the ca. 1.7 kBp long DNA fragment was isolated. Afterwards the PCR fragments were ligated into the ca. 10.7 kBp long BglII/PvuII-YEpL vector fragment (three-fragment ligation). The desired plasmid YEpL/GOD (FIG. 3) was identified by restriction mapping and partially sequenced (cloning junctions).

1.6 Construction of the Plasmid YEpL/GOD-(His)4

The plasmid contains a modified GOD gene which codes for a GOD enzyme variant that has four additional histidine residues at the C-terminus. YEpL/GOD-(His)$_4$ was produced from the plasmid YEpL/GOD.

For this the plasmid YEpL/GOD was partially cleaved with SphI and completely cleaved with PvuII, the ca. 10.7 kBp long SphI/PvuII fragment was isolated and ligated with the following DNA linker prepared from two oligonucleotides (see SEQ ID NO. 9 and SEQ ID NO. 10) by hybridization.

Primer (9): 5'-CAGCACCACCACCACTGACAG-3'

Primer (10): 5'-CTGTCAGTGGTGGTGGTGCTGCATG-3'

```
     SphI
5'-     CAGCACCACCACCACTGACAG-3'
3'-GTACGTCGTGGTGGTGGTGACTGTC-5'
      ----GlnHisHisHisHisStop
```

The desired plasmid YEpL/GOD-(His)4 was identified by colony hybridization using radioactively-labelled primer 10 as the probe and further analyzed by restriction mapping and partial sequencing (C-terminal region of the GOD structural gene).

Example 2

Isolation of Yeast Host Strains with Defective N-glycosylation 2.1 [$^3$H]-mannose Suicide Mutagenesis Principle:

Mutagenesis (starting strain: X2180-1A, genotype: a SUC2 mal mel gal2 CUP1; ATCC 26786)

Incubation with [$^3$H]-mannose

Accumulation of hyperglycosylation-defective mutants by storing the cells at −80° C. until the survival rate of the cells decreases to $10^2$–$10^3$ (2–4 months)

A yeast strain such as X2180-1A (ATCC 26786) is cultured in YEPD medium (2% Bactopeptone, 1% yeast extract, Difco, and 4% glucose), harvested in the logarithmic growth phase (ca. $5\times10^8$ of these cells), washed with 0.1 mol/l sodium phosphate, pH 7 and resuspended in 1.5 ml 0.1 mol/l sodium phosphate, pH 7. The cells are mutagenized by the addition of 0.1 ml ethyl methanesulfonate for 1 hour at 25° C. 0.2 ml of the cells treated in this way is incubated for 10 minutes with 10 ml sodium thiosulfate (5% w/v), washed 3× with 0.1 mol/l sodium phosphate, pH 7.0 and resuspended in YEPD medium (2% Bactopeptone, 1% yeast extract, Difco and 4% glucose).

The cells are incubated at 28° C. while shaking until an OD of 0.6 at 578 nm is achieved. $10^6$ cells are washed with YEP medium (2% Bactopeptone, 1% yeast extract, Difco) and resuspended in 0.1 ml YEP containing 0.1% glucose. 2 mCi [$^3$H]-mannose (specific activity 18.5 Ci/mmol) is added and the culture is incubated for 60 minutes at 28° C. The cells are centrifuged, washed with water and resuspended in YEPD which contains 25% glycerol and stored at −70° C. for the radioactivity to take effect. After ca. 45–50 days when the survival rate of the cells has dropped to 1.5–0.2%, aliquots of the cells are plated on YEP agar plates containing 2% mannose and incubated at 30° C.

2.2 Isolation of Mutants with Reduced N-glycosylation

Mutants with a defect in protein glycosylation are firstly selected for their ability not to incorporate [$^3$H]-mannose and to incorporate [$^{35}$S]-methionine. For this the cells are allowed to grow on YEPD agar plates, the yeast colonies are replicated on 2 Rotband filters (Schleicher & Schell, Dassel, Germany) and the filters are incubated again for 6 hours on YEPD plates. One filter is then incubated in a solution of YEPD (an amount which is just sufficient to wet the filter) which contains 0.01 mCi/ml [$^{35}$S]-methionine. The other filter is impregnated with YEP containing 0.2 mCi/ml [$^3$H]-mannose and incubated for 30 minutes. The cells/colonies are immobilized on the filter with 5% trichloroacetic acid, washed with water and acetone and analyzed by autoradiography.

2.3 Characterization of Positive Clones by Native Gel Electrophoresis of External Invertase The SUC2 gene from *S. cerevisiae* codes for 2 different regulated and compartmented invertase forms, i) a glycosylated invertase which is mainly secreted into the periplasm and ii) an intracellular slightly truncated non-glycosylated form (Carlson, M. et al., Mol. Cell. Biol. 3 (1983) 439–447). Invertase contains 14 potential N-glycosylation sites of which 9–10 are glycosylated on average in the secreted form per invertase subunit. External wild-type invertase migrates as a diffuse band in native gels due to non-uniform outer chain glycosylation. In contrast the cytoplasmic non-glycosylated form yields a sharp band after activity staining. A change in N-glycosylation can thus be crudely analyzed by means of the migration rate and band sharpness of external invertase in native gels.

The yeast strains (X2180-1A wild-type strain and positive clones) were cultured overnight in 5 ml YEPS medium (1% yeast extract, 2% Bactopeptone, Difco and 2% sucrose), the cells were harvested in the late logarithmic growth phase, washed once with 20 mmol/l sodium azide and lysed with glass beads by homogenization in a Whirlmix. The preparation of cell lysate, the native gel electrophoresis and activity staining of invertase with sucrose and 2,3,4-trinitrophenyltetrazolium chloride as substrate/glucose reagent were carried out according to the method of Ballou C. E. (Methods Enzymol. 185 (1990) 440–470).

The positive clones may be divided into 4 classes on the basis of the invertase activity staining:

1. Mutants with wild-type invertase mobility.
2. Mutants that synthesize neither non-glycosylated nor glycosylated invertase.
3. Mutants with defects in outer chain glycosylation (distinct oligomeric band pattern of 3–4 bands).
4. Mutants which lead to a substantial under-glycosylation of invertase (larger mobility than wild-type invertase).

Results

Mutant strains of class 4, designated ngd29 (DSM 7042/7338) and ngd62 (DSM 7160/7340) in the following (ngd stands for "N-glycosylation-defective"), synthesize in comparison to the starting strain X2180-1A a uniformly glycosylated dimeric external invertase (sharp bands and increased migration rate in native gels after activity staining). The ngd mutant strains were osmotically stable, could be cultured at 30° C. and did not aggregate during culture.

Example 3

Construction of Glycosylation-defective Yeast Host Strains for the Expression of Homologous and Heterologous Proteins In order to introduce one or several auxotrophies which can be complemented by transformation, the ngd mutants were crossed with suitable laboratory strains according to the method described by F. Sherman et al. (Methods in Yeast Genetics: A Laboratory Manual, Cold Spring Harbor Laboratory, Cold Spring Harbor, N.Y., (1981)) and diploid strains were isolated by micromanipulation. Subsequently the diploid strains were sporulated and segregants with suitable auxotrophies (e.g. ura3, leu2) and ngd mutation were isolated.

For this the ngd29 mutant was incubated together with the strain DBY746 (MATα ura3-52 leu2-3,-112 trp1-289α his3-α1; [DSM 4316] equivalent to ATCC 44733) and the ngd62 mutant was incubated with the JM1935 strain (MATα ura3 leu2 his4, DMS 7156) for 6 hours at 30° C. in YEPD (1% yeast extract, 2% Bactopeptone, Difco, and 2% glucose). Subsequently zygotes were isolated with the aid of a micromanipulator (model according to de Fonbrune from the Bachhofer Company, Reutlingen, Germany) and grown overnight in 5 ml YEPD. The cells were briefly centrifuged, the medium was decanted until about 0.2 ml remains and the cell pellet was resuspended in the residual medium. This cell suspension was plated on a potassium acetate plate (1% potassium acetate, 1.5% agar). After ca. 5 days the asci obtained in this way were resuspended in 0.5 ml sterile water using an inoculating loop, 10 μl of a β-glucuronidase/aryl sulfatase mixture (Boehringer Mannheim) was added and it was incubated for 10 min at room temperature. Subsequently 10 ml water was added, the ascus suspension was centrifuged and the supernatant was decanted. The spores of several asci were isolated under a micromanipulator and incubated on YEPD plates (YEPD containing 1.5% agar) for 3 days at 30° C. A replica plate was prepared from germinated spores, the colonies were pressed onto synthetic minimal media (0.67% yeast nitrogen base without amino acids, Difco; 2% glucose; 1.5% agar plus additives: 20 mg/l Trp, His, Arg, Met; 30 mg/l Leu, Ile, Lys; 50 mg/l Phe; 100 mg/l Glu, Asp; 400 mg/l Val, Thr, Ser as well as 20 mg/l adenine and uracil; one of these additives was omitted in each of the individual minimal media) and incubated for 3 days at 30° C. Segregants with the ngd29 phenotype which have auxotrophies for uracil and leucine were analyzed/isolated as described in example 2.2. The ngd29 phenotype (as well as the ngd62 phenotype) segregated 2:2 in all examined tetrads, which indicates a single mutation in a single nuclear locus.

Strains BMY3-9A and N-BMY3-9A (MATα leu2-3,-112 ura3-52 his3-Δ1 ngd29; DSM 7042 and DSM 7338) and BMY3-9C and N-BMY3-9C (MATα leu2-3, -112, ura3-52 ngd29; DSM 7193 and DSM 7341) were obtained from the cross DBY746 x ngd29 described here.

Strains BMY12-20D and N-BMY12-20D (MATα leu2 ura3 his4 ngd62; DSM 7160 and DSM 7340) were obtained in an analogous manner from the cross JM1935 x ngd62.

Example 4

Comparison of the Expression/Secretion of Native A. niger GOD and the GOD (His)₄ Variant in Wild-type and Glycosylation-defective Yeast Host Strains The GOD from A. niger is a naturally secreted glycosylated dimeric enzyme. 8 potential N-glycosylation sites (sequons) and 3 cysteine residues two of which form a disulfide bridge are present per subunit. GOD expressed in S. cerevisiae wild-type strains is secreted into the medium and is very heterogeneous with regard to molecular weight due to a non-uniform outer chain glycosylation (hyperglycosylation) (Frederick, K. R. et al., J. Biol. Chem. 265 (1990) 3793–3802; De Baetselier, A. et al., Biotechnology 9 (1991) 559–561; Whittington, H. et al., Curr. Genet. 18 (1990) 531–536). The processed (cleavage of a 22 amino acid long signal sequence) A. niger GOD protein consists of 583 amino acids with a potential molecular weight of 63 273 Da (Frederick, K. R. et al., J. Biol. Chem. 265 (1990) 3793–3802).

The plasmids YEpL/GOD (example 1.5) and YEp/GOD-(His)₄ (example 1.6) were transformed into the wild-type strain JM1935 (MATα leu2 ura3 his4 MAL4) DSM 7156 N-BMY3-9A or BMY3-9A (see example 3) and the transformants were selected on minimal medium agar plates containing 1.5% agarose, 0.67% YNB (yeast nitrogen base, salt-vitamin mixture, Difco) 0.5% CAA (casamino acids, protein hydrolysate, Difco) and 2% fructose as a C-source (uracil selection).

4.1 Culture of the GOD Transformants

In order to amplify the plasmid copy number (selection for the plasmid coded LEU2d allele; Beggs, J. D., Nature 275 (1978) 104–109; Erhart, E. and Hollenberg, C. P. J., Bacteriol. 156 (1983) 625–635) the transformants were streaked on minimal medium plates without leucine (1.5% agarose, 0.67% YNB, Difco, 60 mg/l adenine and 2% fructose).

Precultures were carried out in leucine selective medium containing 0.67% YNB and 4% fructose in shaking flasks at 30° C. for 48 hours and used to inoculate expression cultures (inoculum: 1–2%). The main culture (1 l shaking culture) was incubated at 30° C. in complete medium containing 2% yeast extract, 4% Bactopeptone, Difco, 0.1 mol/l phosphate buffer, pH 7.0, 1% fructose and 6% maltose for 3–4 days while shaking. Samples were taken after 48 and 72 hours and the cell growth (determination of the optical density at 600 nm, $OD_{600}$), the GOD activity secreted into the medium and residual GOD activity in the cells was determined in the crude extract after cell lysis.

| Expression/secretion analysis of GOD in the wild-type strain DSM 7156 and the glycosylation-defective host strains DSM 7042 or DSM 7338 | | | | |
|---|---|---|---|---|
| Plasmid: YEpL/GOD | | | | |
| | GOD activity (U/ml) / Optical density ($OD_{600}$) Time (hours) | | | |
| DSM 7156 | 48 U/ml / $OD_{600}$ | | 72 U/ml / $OD_{600}$ | |
| extracellular | 8 | 13 | 12 | 17 |
| intracellular | 4 | | 6 | |
| total | 12 | | 18 | |
| % secreted | 66 | | 66 | |
| Plasmid YEpL/GOD | | | | |
| | GOD activity (U/ml) / Optical density ($OD_{600}$) Time (hours) | | | |
| DSM 7042/7338 | 48 U/ml / $OD_{600}$ | | 72 U/ml / $OD_{600}$ | |
| extracellular | 11 | 9 | 18 | 14 |
| intracellular | 1 | | 2 | |
| total | 12 | | 20 | |
| % secreted | 87 | | 90 | |

-continued

Expression/secretion analysis of GOD-(His)$_4$ in the wild-
type strain DSM 7156 and the glycosylation-defective
host strains DSM 7042/7338
Plasmid: YEpL/GOD-(His)$_4$ GOD activity (U/ml) / Optical density (OD$_{600}$)
Time (hours)

| DSM 7156 | 48 U/ml / OD$_{600}$ | | 72 U/ml / OD$_{600}$ | |
|---|---|---|---|---|
| extracellular | 8 | 14 | 9 | 14 |
| intracellular | 5 | | 6 | |
| total | 13 | | 16 | |
| % secreted | 62 | | 58 | |

Plasmid: YEpL/GOD

GOD activity (U/ml) / Optical density (OD$_{600}$)
Time (hours)

| DSM 7042/7338 | 48 U/ml / OD$_{600}$ | | 72 U/ml / OD$_{600}$ | |
|---|---|---|---|---|
| extracellular | 12 | 10 | 17 | 13 |
| intracellular | 1 | | 1 | |
| total | 13 | | 18 | |
| % secreted | 88 | | 93 | |

Result

No significant differences were found between the GOD and GOD-(His)$_4$ variant with regard to expression and secretion.

4.2 SDS-PAGE of Secreted GOD

The GOD-(His)$_4$ enzyme expressed (secreted into the medium) in the glycosylation-defective host strains DSM 7042/7338 (ngd29) and DSM 7160/7340 (ngd62) together with the enzyme expressed (secreted) in the wild-type strain DSM 7156 and purified GOD from A. niger (Boehringer Mannhein, GFR) were further characterized by SDS-PAGE and subsequent protein staining. The medium supernatants from the wild-type strain containing GOD were concentrated 10-fold by TCA precipitation before electrophoresis. Carbohydrate-free GOD-(His)$_4$ enzyme was prepared enzymatically using N-glycosidase F and used as a standard for size.

Enzymatic Deglycosylation with N-glycosidase F

The deglycosylation was carried out according to the method published by Haselbeck, A. and Hösel, W. (Topics in Biochemistry 8 (1988) 1–4). 0.1 ml medium supernatant containing GOD-(His)$_4$ was precipitated with trichloroacetic acid (final concentration: 10%), the precipitated proteins were centrifuged, the protein pellet was washed with 70% ethanol, dried in a vacuum, taken up in 10 μl 20 mmol/l potassium phosphate buffer, pH 7.2 containing 1% SDS and heated for 3 min. to 95° C. After cooling to room temperature the sample was diluted to 0.1 ml with 20 mmol/l potassium phosphate buffer, pH 7.2, octylglucoside (final concentration: 0.5%) and 5 units N-glycosidase F, incubated for 1–12 hours at 37° C. and subsequently 25 μl 5×SDS buffer (see above) was added.

Result

The GOD enzymes (GOD and GOD-(His$_4$)) expressed in the glycosylation-defective ngd mutant strains are visible in SDS-PAGE gels after protein staining as dominant uniform bands with a molecular weight of ca. 80 kDa. This experiment shows the absence of outer chain glycosylation in the GOD enzymes and indicates a uniform core-like glycosylation. With regard to glycosylation the ngd mutant strains have a mnn9-like phenotype. In contrast the GOD enzymes expressed in wild-type strains are only recognizable as very diffuse bands which cover a molecular weight range of ca. 80–200 kDa.

Example 5

Characterization of the N-glycosylation-defective
ngd Mutants on the Basis of Growth on YEPD
Agar Plates Containing Orthovanadate or
Hygromycin B Glycosylation-defective mutants such as e.g. mnn8, mnn9 and mnn10 show an increased resistance to orthovanadate and an increased sensitivity to the antibiotic hygromycin B. The resistance/sensitivity phenotype enables a differentiation/classification of N-glycosylation-defective mutants (Ballou, L. et al., Proc. Natl. Acad. Sci. 88 (1991) 3209–3212).

The strains to be examined were cultured overnight in YEPD medium (5 ml roller culture) and the strains/cultures were adjusted to an optical density (OD$_{600}$) of exactly 0.05 with YEPD medium. Afterwards 20 μl of each cell suspension was spotted on YEPD agar plates containing 2–15 mmol/l sodium orthovanadate or 10–200 μg/ml hygromycin B. The growth of the cell spots was evaluated after 2 days incubation at 30° C. (see table).

Growth phenotype of yeast cells on YEPD agar Plates
containing sodium orthovanadate or hygromycin B

| Strain | Orthovanadate resistance mmol/l | | | | | | | | Hygromycin resistance (μg/ml) | | | |
|---|---|---|---|---|---|---|---|---|---|---|---|---|
| | 2 | 3 | 4 | 5 | 6 | 7 | 10 | 15 | 10 | 50 | 100 | 200 |
| DBY 746 (wild-type) | + | + | + | + | − | − | − | − | + | + | − | − |
| X2180-1A (wild-type) | + | + | + | + | − | − | − | − | + | + | − | − |
| LB347-1C (mnn9)[1] | + | + | + | + | + | + | + | + | − | − | − | − |
| BMY3-9A (ngd29) | + | + | + | + | + | − | − | − | + | ± | − | − |
| BMY12-20D (ngd62) | + | + | + | ± | − | − | − | − | + | ± | − | − |
| N-BMY3-9A (ngd29) | + | + | + | + | + | − | − | − | + | ± | − | − |
| N-BMY12-20D (ngd62) | + | + | + | ± | − | − | − | − | + | ± | − | − |

+ growth
± very slow growth
− no growth
[1] J. Biol. Chem. 259 (1984) 3805–3811

Result

There are differences between the ngd mutants with regard to resistance pattern which differs from that of the mnn9 mutant and wild-type strains.

Example 6

Characterization/Identification of ngd Mutants (Allelism Test)

An allelism test serves to identify (differentiate between) genes and gene defects (mutations). With this technique it is possible to analyze whether 2 mutants are allelic (have a mutation in the same gene). The ngd mutants were examined for allelism among each other and to the mnn9 mutant.

The allelism tests were carried out by means of genetic standard techniques (see: Sherman, F.; Fink, G. R.; Hicks, J. B., Methods in Yeast Genetics: A Laboratory Manual. Cold Spring Harbor Laboratory, Cold Spring Harbor, N.Y., (1981); Guthrie, C. and Fink, G. R. (eds.), Guide to Yeast Genetics and Molecular Biology. Methods Enzymol. 194 (1991)).

Principle:

Two haploid mutant strains to be analyzed of different pairing type with auxotrophy requirements that complement each other are crossed and the diploid strains are selected on plates with minimal medium. The diploidism of the isolated strains is confirmed by the presence of DNA sequences specific for the a and α pairing type using PCR analysis in accordance with the method of Huxley, C. et al. (Trends Genet. 6 (1990) 236).

Two mutants are allelic, i.e. have a mutation in the same gene, when the mutations do not complement each other in the diploid cell.

Two mutants are not allelic, i.e. have a mutation in two different genes, when the mutations complement each other in the diploid cell and a wild-type phenotype results.

Strains used:

His and Trp were omitted in the individual minimal media as stated in the table in the column headed "Selection of diploids".

Result:

The mutants ngd29 and ngd62 differ from one another and are different from mnn9 (non-allelic).

Example 7

Isolation of GOD and GOD-(His)$_4$ from Wild-type and Hyperglycosylation-defective Yeast Strains 7.1 Isolation of GOD-(His)$_4$ by means of Metal Chelate Chromatography The GOD variant GOD-(His)$_4$ was isolated using this isolation method from the culture filtrate of BMY3-9A/GOD-(His)$_4$ cells and BMY12-20D/GOD-(His)$_4$ cells (hyperglycosylation-defective host strains).

The culture filtrate was titrated to pH 7.5 with sodium hydroxide solution and applied to a NTA column equilibrated with 10 mmol/l potassium phosphate buffer, pH 7.5 (column volume 25 ml; NTA gel from the Diagen Company, Düsseldorf; Hochuli, E. et al., J. Chromatography 411 (1987) 177–184; Hochuli, E. et al., Biotechnology 6 (1988) 1321–1325). The column was rewashed with 5–10 column volumes 1 mol/l sodium chloride in 10 mmol/l potassium phosphate buffer, pH 7.5, and with 5–10 column volumes 10 mmol/l potassium phosphate buffer, pH 7.5. Afterwards the GOD-(His)$_4$ enzyme was eluted with 0.1 mol/l imidazole in equilibration buffer, pH 7.5 and the fractions containing GOD-(His)$_4$ (yellow) were dialysed against 10 mmol/l potassium phosphate buffer, pH 7.5.

7.2 Isolation of GOD and GOD Variants by Ion Exchange Chromatography on Q-Sepharose ff After Previous Concentration and Dialysis Native GOD and hyperglycosylated GOD were purified according to this method.

| Strain | DSM |
|---|---|
| BMY3-9C (MATα leu2-3,-112 ura3-52 ngd29) | DSM 7193 |
| BMY8-12A (MATa trp1-289$^a$ his3-Δ1 ngd62) | DSM 7157 |
| BMY13-1C (MATα ura3-52 leu2-3,-112 his3-Δ1 mnn9) | DSM 7159 |
| BMY13-7B (MATa leu2-3,-112 his3-Δ1 mnn9) | DSM 7158 |
| BMY12-20D (MATα leu2 ura3 his4 ngd62) | DSM 7160 |
| N-BMY3-9C (MATα leu2-3,-112 ura3-52 ngd29) | DSM 7341 |
| N-BMY13-1C (MATα ura3-52 leu2-3,-112 his3-Δ1 mnn9) | DSM 7339 |
| BMY12-20D (MATα leu2 ura3 his4 ngd62) | DSM 7340 |

| Crossing partners MATα MATa | Phenotype of the haploids | Selection diploids | Phenotype of the diploids |
|---|---|---|---|
| BMY3-9C × BMY8-12A | ngd29xngd62 | his leu | wild-type |
| BMY3-9C × BMY13-7B | ngd29xmnn9 | his ura | wild-type |
| BMY13-1C × BMY8-12A | mnn9xngd62 | trp ura | wild-type |
| BMY12-20D × BMY13-7B | ngd62xmnn9 | his | wild-type |
| N-BMY3-9C × BMY8-12A | ngd29xngd62 | his leu | wild-type |
| N-BMY3-9C × BMY13-7B | ngd29xmnn9 | his ura | wild-type |
| N-BMY13-1C × BMY8-12A | mnn9xngd62 | trp ura | wild-type |
| N-BMY12-20D × BMY13-7B | ngd62xmnn9 | his | wild-type |

SC=synthetic complete medium (0.67% yeast nitrogen base without amino acids, Difco; 2% glucose; 1.5% agar plus additives: 20 mg/l Trp, His, Arg, Met; 30 mg/l Leu, Ile, Lys; 50 mg/l Phe; 100 mg/l Glu, Asp; 400 mg/l Val, Thr, Ser as well as 20 mg/l adenine and uracil; the amino acids Ura, 33 g solid ammonium sulfate (AS saturation concentration 55%) was added to 100 ml sterile-filtered culture filtrate while stirring slowly, the precipitated proteins were centrifuged down after 1–2 hours incubation at room temperature, dissolved in 25 ml 25 mmol/l potassium phosphate buffer, pH 7.5 and dialysed against the same buffer (4×10 1, 24 hours, 4° C.).

Subsequently the dialysate was applied to a Q-Sepharose ff column (column volume 12 ml) equilibrated with 25 mmol/l potassium phosphate buffer, pH 7.5 and rewashed with 5–10 column volumes equilibration buffer. The bound GOD enzymes were eluted by a gradient of 0–1 mol/l KCl in equilibration buffer (ca. 10 column volumes) and the fractions containing GOD (yellow) were pooled.

Example 8

Biochemical Characterization of the Isolated GOD Enzymes

8.1 Determination of the Specific GOD Activity

The determination of GOD activity is carried out as described in the "general methods" section.

Specific activity of GOD and GOD-$(His)_4$ expressed in
*A. niger*, *S. cerevisiae* (wild-type) and *S. cerevisiae*
(hyperglycosylation-defective mutants)

| Enzyme | Organism/ glycosylation | spec. activity (U/mg protein) | spec. activity (U/mg enzyme) |
|---|---|---|---|
| GOD | (*A. niger*) | 225 | 195 |
| GOD | (WT) | 230 | 69 |
| GOD | (ngd29) | 228 | 196 |
| GOD | (ngd62) | 213 | 220 |
| GOD-$(His)_4$ | (WT) | 220 | 68 |
| GOD-$(His)_4$ | (ngd29) | 223 | 200 |
| GOD-$(His)_4$ | (ngd62) | 230 | 225 |

*A. niger*, GOD from *A. niger*, purity II (Boehringer Mannheim)
WT, *S. cerevisiae* wild-type
ngd29, *S. cerevisiae* hyperglycosylation-defective ngd29 mutant
ngd62, *S. cerevisiae* hyperglycosylation-defective ngd62 mutant

8.2 Determination of Molecular Weight by SDS Polyacrylamide Gel Electrophoresis (SDS-PAGE)

The purified GOD enzymes were admixed with 1/5 volumes 5×SDS sample buffer (1×SDS sample buffer: 50 mmol/l Tris-HCl, pH 6.8, 1% SDS, 1% mercaptoethanol, 10% glycerol, 0.001% bromophenol blue) and incubated for 5 min at 95° C. Afterwards the proteins were separated by SDS-PAGE (Laemmli, U. K., Nature 227 (1970) 680–685) and stained with Coomassie Brilliant BlueR dye.

Molecular weight/subunit after SDS-PAGE of GOD and GOD-$(His)_4$ expressed in *A. niger*, *S. cerevisiae* (wild-type) and *S. cerevisiae* hyperglycosylation-defective mutants.

| Enzyme | Organism/ glycosylation | Molecular weight/subunit (kDa) |
|---|---|---|
| GOD | (*A. niger*) | ca. 80 |
| GOD | (WT) | 80–140 |
| GOD | (ngd29) | ca. 80 |
| GOD | (ngd62) | ca. 80 |
| GOD-$(His)_4$ | (WT) | 80–140 |
| GOD-$(His)_4$ | (ngd29) | ca. 80 |
| GOD-$(His)_4$ | (ngd62) | ca. 80 |

*A. niger*, GOD from *A. niger*, purity II (Boehringer Mannheim)
WT, *S. cerevisiae* wild-type
ngd29, *S. cerevisiae* hyperglycosylation-defective ngd29 mutant
ngd62, *S. cerevisiae* hyperglycosylation-defective ngd62 mutant

8.3 Determination of the Portion of Carbohydrate (Anthrone Reaction)

The carbohydrate portion of the GOD enzymes from different organisms and yeast strains was determined following the method of Ashwell, G. (Methods Enzymol. 3 (1957) 84).

For this 0.5 ml purified GOD enzyme (concentration 20–100 U/ml in $H_2O$) was mixed with 5 ml anthrone reagent, the solution was incubated for 5 minutes at 25° C. and afterwards heated for 15 minutes in a boiling water bath. After the sample had been cooled to 25° C. the absorbance was determined at 630 nm against a reagent blank. The portion of carbohydrate in the GOD sample was determined by means of a mannose calibration curve with mannose standard solutions of 5, 25, 75 and 100 µg/ml mannose which was set up at the same time.

Preparation of the Anthrone Reagent:

66 ml concentrated sulfuric acid is carefully diluted with 34 ml water. After cooling to 80° C., 50 mg anthrone and 1 g thiourea are dissolved in the sulfuric acid. The anthrone reagent can be stored for two weeks at 4° C.

Carbohydrate Portion of GOD and GOD-$(His)_4$ expressed in
*A. niger*, *S. cerevisiae* (wild-type) and *S. cerevisiae*
(hyperglycosylation-defective mutants)

| Enzyme | Organism/ glycosylation | Carbohydrate portion (%) (relative to protein) |
|---|---|---|
| GOD | (*A. niger*) | 13 |
| GOD | (WT) | 71 |
| GOD | (ngd29) | 12.5 |
| GOD | (ngd62) | 13 |
| GOD-$(His)_4$ | (WT) | 65 |
| GOD-$(His)_4$ | (ngd29) | 11 |
| GOD-$(His)_4$ | (ngd62) | 12 |

*A. niger*, GOD from *A. niger*, purity II (Boehringer Mannheim)
WT, *S. cerevisiae* wild-type
ngd29, *S. cerevisiae* hyperglycosylation-defective ngd29 mutant
ngd62, *S. cerevisiae* hyperglycosylation-defective ngd62 mutant

8.4 Determination of the Km Value

The Km value of the various GOD enzymes was determined according to the instructions of Michal, G., Methods of Enzymatic Analysis, Vol. 1, Bergmeyer, H. U. (ed.) "Verlag Chemie Weinheim", Academic Press, New York and London, pp. 144–156 (1974).

Km value of GOD and GOD-$(His)_4$ expressed in *A. niger*,
*S. cerevisiae* (wild-type) and *S. cerevisiae* (ngd29)
mutant

| Enzyme | Organism/ glycosylation | Km [mol × $l^{-1}$] |
|---|---|---|
| GOD | (*A. niger*) | 0.03 |
| GOD | (WT) | 0.03 |
| GOD | (ngd29) | 0.03 |
| GOD-$(His)_4$ | (WT) | 0.03 |
| GOD-$(His)_4$ | (ngd29) | 0.03 |

*A. niger*, GOD from *A. niger*, purity II (Boehringer Mannheim)
WT, *S. cerevisiae* wild-type
ngd29, *S. cerevisiae* hyperglycosylation-defective ngd29 mutant

8.6 Determination of the Thermostability of GOD and GOD-(His)₄ Expressed in *A. niger*, *S. cerevisiae* (Wild-type) and *S. cerevisiae* (ngd29 Mutant)

The thermostability of the various GOD enzymes was determined by differential scanning calorimetry (DSC). For this the denaturation point (Tm) of the GOD enzymes was determined in a defined solvent (H$_2$O), at a defined GOD protein concentration (20 mg/ml) and defined heating rate (10° C./min) (see Table).

Tm value (from DSC spectra) of GOD and GOD-(His)$_4$ secreted in *A. niger* and *S. cerevisiae* (ngd29 mutant)

| Enzyme | Organism/glycosylation | differential scanning calorimetry Tm value (°C.) |
|---|---|---|
| GOD | (*A. niger*) | 68.5 |
| GOD | (ngd29) | 74.7 |
| GOD-(His)$_4$ | (ngd29) | 75.8 |

*A. niger*, GOD from *A. niger*, purity II (Boehringer Mannheim)
ngd29, *S. cerevisiae* hyperglycosylation-defective ngd29 mutant Residual GOD Activity After a Thermal Stress at 55° C. of GOD and GOD-(His)$_4$ Expressed in *A. niger* and *S. cerevisiae* (ngd29 Mutant)

In order to determine the thermostability, the various GOD enzymes were incubated at 55° C. at a concentration of 25 U/ml in 0.2 mol/l sodium phosphate buffer, pH 7.5 and after 2 hours the residual GOD activity was determined as described in the general methods section.

Residual GOD activity after a thermal stress of GOD and GOD-(His)$_4$ expressed in *A. niger*, *S. cerevisiae* (wild-type) and *S. cerevisiae* (ngd29 mutant)

| Enzyme | Organism/glycosylation | Residual activity in % after 2 h stress at 55° C. |
|---|---|---|
| GOD | (*A. niger*) | 5 |
| GOD | (WT) | 40 |
| GOD | (ngd29) | 40 |
| GOD-(His)$_4$ | (ngd29) | 41 |

*A. niger*, GOD from *A. niger*, purity II (Boehringer Mannheim)
WT, *S. cerevisiae* wild-type
ngd29, *S. cerevisiae* hyperglycosylation-defective ngd29 mutant

8.7 Determination of the pH Stability of GOD and GOD-(His)₄ Expressed in *A. niger* and *S. cerevisiae* (ngd29 Mutant)

The pH stability of the various GOD enzymes is determined by means of DSC. For this the denaturation point (Tm) of the GOD enzymes was determined in relation to the pH value in a defined solvent (100 mmol/l citrate buffer for pH values of 3.5–6.5 and 100 mmol/l borate buffer for pH values of 7.5–9.5) at a defined GOD protein concentration (25 mg/ml) and a defined heating rate (10° C./minute).
Result:
GOD and GOD-(His)$_4$ isolated from the hyperglycosylation-defective ngd29 mutant behaves like native *Aspergillus niger* GOD with respect to pH stability.
Publications:

Bekkers, A. C. A. P. A.; Franken, P. A. F.; Van den Bergh, C. J.; Verbakel, J. M. A.; Verheij, H. M.; De Haas, G. H.: The use of genetic engineering to obtain efficient production of porcine pancreatic phospholipase A2 by *Saccharomyces cerevisiae*. Biochim. Biophys. Acta 1089, 345–351 (1991).

Ballou, L.; Cohen, R. E.; Ballou, C. E.: *Saccharomyces cerevisiae* mutants that make mannoproteins with a truncated carbohydrate outer chain. J. Biol. Chem. 255, 5986–5991 (1980).

Ballou, C. E.: Yeast cell wall and cell surface. In: Strathern, J. N.; Jones, E. W.; Broach, J. R. (eds.), The Molecular Biology of the Yeast Saccharomyces, Metabolism and Gene Expression, Cold Spring Harbor Laboratory, New York, pp. 335–360 (1982).

Ballou, L.; Alvarado, E.; Tsai, P.; Dell, A; Ballou, C. E.: Protein glycosylation defects in the *Saccharomyces cerevisiae* mnn7 mutant class. J. Biol. Chem. 264, 11857–11864 (1989).

Ballou, C. E.: Isolation characterization, and properties of *Saccharomyces cerevisiae* mmn mutants with nonconditional protein glycosylation defects. Methods Enzymol. 185, 440–470 (1990).

Ballou, L.; Hitzeman, R. A.; Lewis, M. S.; Ballou, C. S.: Vanadate-resistant yeast mutants are defective in protein glycosylation. Proc. Natl. Acad. Sci. 88, 3209–3212 (1991).

Beggs, J. D.: Transformation of yeast by a replicating hybrid plasmid. Nature 275, 104–109 (1978).

Carlson, M.; Taussig, R.; Kustu, S.; Botstein, D.: The secreted form of invertase in *Saccharomyces cerevisiae* is synthesized from mRNA encoding a signal sequence. Mol. Cell. Biol. 3, 439–447 (1983).

Ciriacy, M.: Genetics of alcohol dehydrogenase in *Saccharomyces cerevisiae*. I. Isolation and genetic analysis of adh-mutants. Mut. Res. 29, 315–326 (1975). De Baetselier, A.; Vasavada, A.; Dohet, P.; Ha-Ti, V.; De Beukelaer, M.; Erpicum, T.; De Clerk, L.; Hanotier, J.; Rosenberg, S.: Fermentation of yeast producing *A. niger* glucose oxidase: scale up, purification and characterization of the recombinant enzyme. Biotechnology 9, 559–561 (1991).

Delorme, E.: Transformation of *Saccharomyces cerevisiae* by electroporation. Applied and Environmental Microbiology 55, 2242–2246 (1989).

Dijken, J. P. van; Veenhuis M.: Cytochemical localization of glucose oxidase in peroxisomes of *Aspergillus niger*. European J. Appl. Microbiol. Biotechnol. 9, 275–283 (1980)

Erhart, E.; Hollenberg, C. P.: The presence of a defective LEU2 gene on 2μDNA recombinant plasmids of *Saccharomyces cerevisiae* is responsible for curing and high copy number. J. Bacteriol. 156, 625–635 (1983).

Frederick, K. R.; Tung, J.; Emerick, R. S.; Masiarz, F. R.; Chamberlain, S. H.; Vasavada, A.; Rosenberg, S.; Chakraborty, S.; Schopter, L. M.; Massey, N.: Glucose oxidase from *Aspergillus niger*. J. Biol. Chem. 265, 3793–3802 (1990).

Hadwick, K. G.; Lewis, M. J.; Semenza, J.; Dean, N.; Pelham, H. R. B.: ERD1, a yeast gene required for the retention of luminal endoplasmic reticulum proteins, affects glycoprotein processing in the Golgi apparatus. EMBO J. 9, 623–630 (1990).

Haselbeck, A.; Hösel, W.: Studies on the effect of the incubation conditions, various detergents and protein concentration on the enzymatic activity of N-glycosidase F (glycopeptidase F) and endoglycosidase F. Topics in Biochemistry 8, 1–4 (1988).

Hochuli, E.; Doebeli, H.; Schacher, A.: New metal chelate adsorbent selective for proteins and peptides containing neighbouring histidine residues. J. Chromatography 411, 177–184 (1987).

Hochuli, E.; Bannwarth, W.; Doebeli, H.; Genz, R.; Stueber, D.: Genetic approach to facilitate purification of recombinant proteins with a novel metal chelate adsorbent. Biotechnology 6, 1321–1325 (1988).

Huffaker, T. C.; Robbins, P. W.: Yeast mutants deficient in protein glycosylation. Proc. Natl. Acad. Sci. 80, 7466–7470 (1983).

Innis, M. A.: Glycosylation of heterologous proteins in *Saccharomyces cerevisiae*. In: Barr, P. J.; Brake, A. J.; Valenzuela, P. (eds.), Yeast genetic engineering, Butterworths, Stoneham, Mass., pp. 233–246 (1989).

Ito, H.; Jukuda, A.; Murata, K.; Kimura, A: Transformation of intact yeast cells treated with alkali cations. J. Bacteriol. 153, 163–168 (1983).

Kopetzki, E.; Buckel, P.; Schumacher, G.: Cloning and characterization of baker's yeast alpha glucosidase: overexpression in a yeast strain devoid of vacuolar proteinases. Yeast 5, 11–24 (1989).

Kornfeld, R.; Kornfeld, S.: Assembly of asparagine-linked oligosaccharides. Ann. Rev. Biochem. 54, 631–664 (1985).

Kukuruzinska, M. A.; Bergh, M. L. E.; Jackson, B. J.: Protein glycosylation in yeast. Ann. Rev. Biochem. 56, 915–944 (1987).

Kriechbaum, M.; Heilmann, H, J.; Wientjes, F. J.; Hahn, M.; Jany, K.-D.; Gassend H. G.; Sharif, F.; Alaeddinoglu, G.: Clonig and DNA sequence analysis of the glucose oxidase gene from *Aspergillus niger* NRRL-3. FEBS Lett. 255, 63–66 (1989).

Laemmli, U. K.: Cleavage of structural proteins during the assembly of the head of bacteriophage T4. Nature 227, 680–685 (1970).

Maniatis, T. et al., In: Molecular cloning: A laboratory manual. Cold Spring Harbor Laboratory Press, Cold Spring Harbor, N.Y., (1989).

Moir, D. T.: Yeast mutants with increased secretion efficiency. In: Barr, P. J.; Brake, A. J.; Valenzuela, P. (eds.), Yeast genetic engineering, Butterworths, Stoneham, Mass., pp. 215–231 (1989).

Mullis, K. B.; Faloona, F. A.: Specific synthesis of DNA in vitro via a polymerase-catalyzed chain reaction. Methods Enzymol. 155, 355–350 (1987).

Nakano, A.; Muramatsu, M.: A novel GTP-binding protein, Sarp1, is involved in transport from the endoplasmic reticulum to the Golgi apparatus. J. Cell. Biol. 109, 2677–2691 (1989).

Newman, A. P.; Ferro-Novick, S.: Characterization of new mutants in the early part of the yeast secretory pathway isolated by [3H]mannose suicide selection. J. Cell. Biol. 105, 1587–1594 (1987).

Novick, P.; Field, C.; Schekman, R.: Identification of 23 complementation groups required for post-translational events in the yeast secretory pathway. Cell 21, 205 215 (1980).

Paulson, C. P.: Glycoproteins: what are the sugar chains for? TIBS 14, 272–276 (1989).

Rudolph, H. K., Antebi, A.; Fink, G. R.; Buckley, C. M.; Dorman, T. E.; LeVitre, J.; Davidow, L. S.; Mao, J.; Moir, D. T.: The yeast secretory pathway is perturbed by mutations in PMR1, a member of a Ca2+ ATPase family. Cell 58, 133–145 (1989).

Reddy, V. A.; Johnson, R. S.; Biemann, K.; Williams, R. S.; Ziegler, F. D.; Trimble, R. B.; Maley, F.: Characterization of glycosylation sites in yeast external invertase. I. N-linked oligosaccharide content of the individual sequons. J. Biol. Chem. 263, 6978–6985 (1988).

Runge, K. W.; Robbins, P. W.: *Saccharomyces cerevisiae* mutants in the early stages of protein glycosylation. In: Bonventre, P. F.; Morello, J. A. M.; Silver, S. D.; Wu, H. C. (eds.), Microbiology-1986. American Society for Microbiology, Washington, D.C. pp. 312–316 (1986).

Schekman, R.; Novick, P.: The secretory process and yeast cell-surface assembly. In: Strathern, J. N.; Jones, E. W.; Broach, J. R. (eds.), The Molecular Biology of the Yeast Saccharomyces, Metabolism and Gene Expression, Cold Spring Harbor Laboratory, New York, pp. 361–398 (1982).

Schmitt, H. D.; Wagner, P.; Pfaff, E.; Gallwitz, D.: The ras-related YPT1 gene product in yeast: a GTP-binding protein that might be involved in microtubule organization. Cell 47, 401–412 (1986).

Schmitt, H. D.; Puzichia, M.; Gallwitz, D.: Study of a temperature-sensitive mutant of the ras-related YPT1 gene product in yeast suggests a role in the regulation of intracellular calcium. Cell 53, 635–647 (1988).

Sherman, F.; Fink, G. R.; Hicks, J. B.: Methods in Yeast Genetics: A Laboratory Manual, Cold Spring Harbor Laboratory, Cold Spring Harbor, N.Y., (1981).

Tanner, W.; Lehle, L.: Protein glycosylation in yeast. Biochim. Biophys. Acta 906, 81–99 (1987).

Warren, C. E.: Glycosylation- considerations for protein engineering. BFE 7, 392–395 (1990).

Whittington, H.; Kerry-Williams, S.; Bidgood, K.; Dodsworth, N. Peberdy, J.; Dobson, M.; Hinchliffe, E.; Ballance, D. J.: Expression of the *Aspergillus niger* glucose oxidase gene in *A. niger, A. nidulans* and *Saccharomyces cerevisiae*. Curr. Genet. 18, 531–536 (1990).

Zamenhof, S.: Preparation and assay of deoxyribonucleic acid from animal tissue. Methods Enzymol. 3, 696–704 (1957).

Ziegler, F. D.; Maley, F.; Trimble, R. B.: Characterization of glycosylation sites in yeast external invertase. II. Location of the endo-betta-N-acetylglucosaminidase H-resistant sequons. J. Biol. Chem. 263, 6978–6985 (1988).

Duncan, M. J.; Smith, R. A.: Supersecreting mutants of *Saccharomyces cerevisiae*. EP-A 0 201 208, Collarborative Research Inc., Fink, G. R.: Improved supersecreting mutants of *Saccharomyces cerevisiae*. EP-A 0 382 332, Collaborative Research Inc., Knisker, P. J.; Hagopian, A.; Miller, W. J.; Yamazaki, S.; Ellis, R. W.: Method for producing nonhyperglycosylated hepatitis B virus protein. EP-A 0 344 864, Merck & Co. Inc., Kopetzki, E.; Schumacher, G.; Zimmermann, F. K.: "Expressionsvektor und Verfahren zur regulierten Herstellung von Proteinen in Eukaryonten". EP-A 0 323 838, Boehringer Mannheim GmbH, MacKay, V. L.; Welch, S. K.; Yip, C. L.: Methods of regulating protein glycosylation. EP-A 0 314 096, Zymogenetics Inc.

Rosenberg, S.: Production of glucose oxidase in recombinant systems.

We claim:

1. Recombinant glucose oxidase obtainable from *A. niger* having a molecular weight of about 68–80 kDa, a specific activity of about 200 U/mg enzyme plus carbohydrate, a carbohydrate portion of about 12% and a residual activity of at least 30% after incubation for two hours at a temperature of 55° C.

2. A method of producing recombinant glucose oxidase comprising transforming N-glycosylation deficient yeast cells selected from the group consisting of DSM 7042, DSM 7338, DSM 7160 and DSM 7340 with a nucleic acid molecule from *A. niger* which encodes glucose oxidase and culturing said transformed yeast cells under conditions which allow for the production of glucose oxidase.

* * * * *

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

ATTTCTCCTT ATTGCGCGCT T                                     21

( 2 ) INFORMATION FOR SEQ ID NO: 2:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

TCTATTCAGC TGTCGACATA GATCTTATGT AATTTAGTTA CGCTTGAC        48

( 2 ) INFORMATION FOR SEQ ID NO: 3:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

AGATCTATGT CGACAGCTGA ATAGATAAAA TTAGTGCGGA CTTTTTTTTA      50

( 2 ) INFORMATION FOR SEQ ID NO: 4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

GTCATTTGTA AAGTAAAATT CCAA                               24

( 2 ) INFORMATION FOR SEQ ID NO: 5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GCCCGGTACC AGATCTATGC AGACTCTCCT TGTGAGCT                38

( 2 ) INFORMATION FOR SEQ ID NO: 6:

( i ) SEQUENCE CHARACTERISTICS:

(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 6:

TCTAGAACTA GTGGATCCCC C    21

(2) INFORMATION FOR SEQ ID NO: 7:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 7:

GCCGGCGAAC GTGGCGAGAA    20

(2) INFORMATION FOR SEQ ID NO: 8:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO: 8:

ATATATCAGC TGTCACTGCA TGCTAGCATA ATCTTCCAAG ATAGC    45

(2) INFORMATION FOR SEQ ID NO: 9:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 9:

CAGCACCACC ACCACTGACA G    21

(2) INFORMATION FOR SEQ ID NO: 10:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 10:

CTGTCAGTGG TGGTGGTGCT GCATG    25